United States Patent [19]

Lockwood, Jr.

[11] Patent Number: 5,403,286

[45] Date of Patent: Apr. 4, 1995

[54] HYPODERMIC NEEDLE SAFETY DEVICE WITH SLIDING OUTER COVER

[76] Inventor: Hanford N. Lockwood, Jr., 2222 Alameda De Las Pulgas, San Mateo, Calif. 94403

[21] Appl. No.: 151,090

[22] Filed: Nov. 12, 1993

Related U.S. Application Data

[62] Division of Ser. No. 967,651, Oct. 28, 1992, Pat. No. 5,295,975.

[51] Int. Cl.6 ............................................. A61M 5/00
[52] U.S. Cl. ................................ 604/110; 604/198; 128/763
[58] Field of Search ............... 604/110, 192, 198, 263, 604/187; 128/763, 764, 765

[56] References Cited

U.S. PATENT DOCUMENTS

| | | |
|---|---|---|
| 4,170,993 | 10/1979 | Alvarez . |
| 4,425,120 | 1/1984 | Sampson et al. . |
| 4,643,199 | 2/1987 | Jennings, Jr. et al. . |
| 4,693,708 | 9/1987 | Wanderer et al. . |
| 4,695,274 | 9/1987 | Fox . |
| 4,702,738 | 10/1987 | Spencer . |
| 4,723,943 | 2/1988 | Spencer . |
| 4,731,059 | 3/1988 | Wanderer et al. ............ 604/198 X |
| 4,804,371 | 2/1989 | Vaillancourt . |
| 4,894,055 | 1/1990 | Sudnak ............................ 604/198 |
| 4,946,446 | 8/1990 | Vadher ............................ 604/198 |
| 4,966,592 | 10/1990 | Burns et al. . |
| 5,011,479 | 4/1991 | Le et al. ......................... 604/198 |
| 5,066,287 | 11/1991 | Ryan ............................ 128/763 X |
| 5,098,403 | 3/1992 | Sampson . |
| 5,104,384 | 4/1992 | Parry ............................. 604/192 |
| 5,152,751 | 10/1992 | Kozlowski . |

*Primary Examiner*—John D. Yasko
*Attorney, Agent, or Firm*—Townsend and Townsend Khourie and Crew

[57] ABSTRACT

A safety device for preventing accidental injury from hypodermic needles comprises an extension for attachment to a standard medical syringe. A standard hypodermic needle attaches to the opposite end of the extension and the extension has an inner cavity for conveying fluid between the syringe and the needle. An outer cover is disposed about the extension for sliding along the length of the extension to cover the needle. The safety device is easily modified to perform as a system for collecting blood or other fluid from a patient by adding a special needle and a blood collection holder at the back end of the extension. In this configuration, the outer cover guards the standard needle and the blood collection holder covers the special needle to prevent accidental injury or disease transmission.

8 Claims, 4 Drawing Sheets

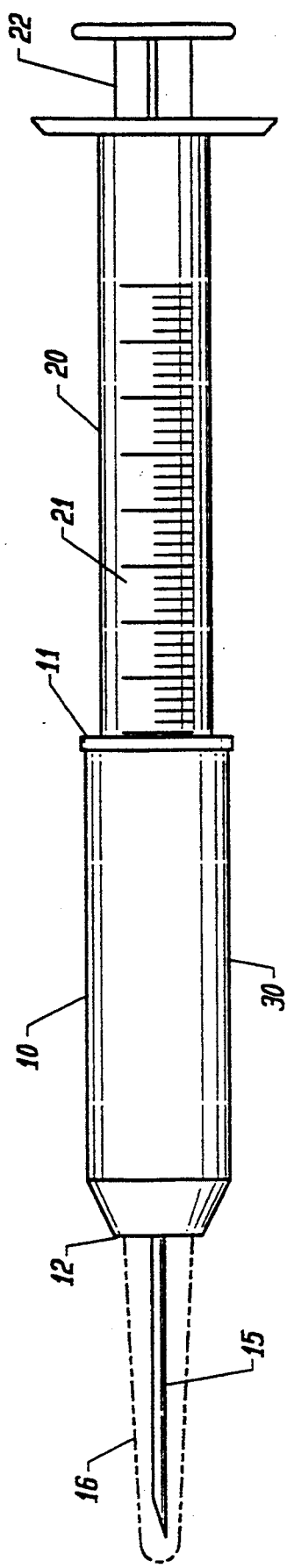
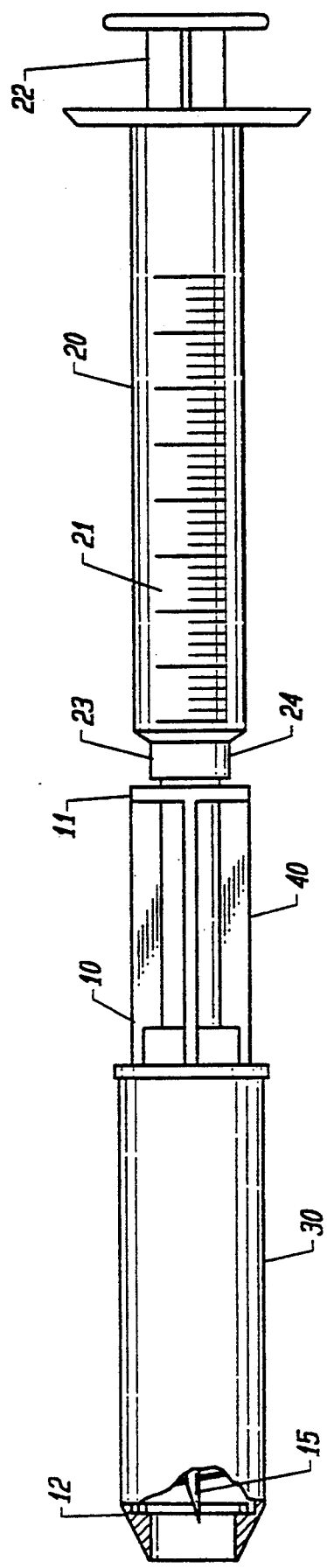

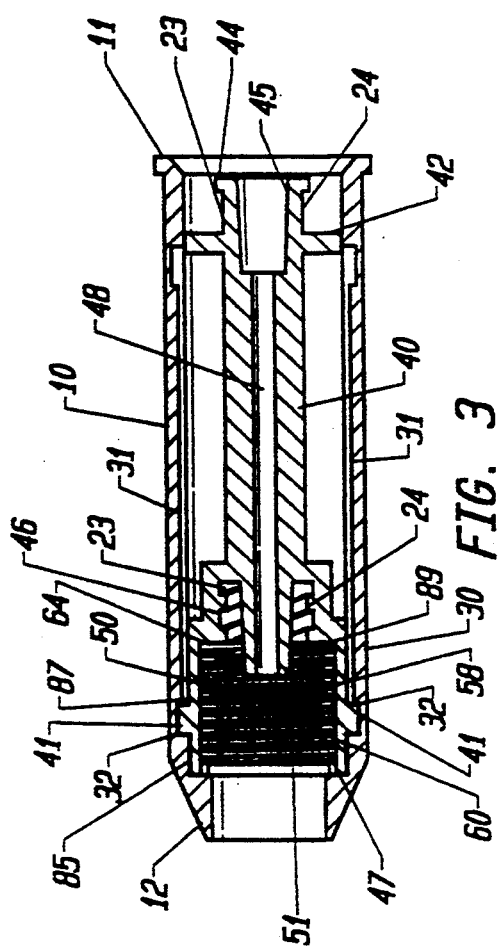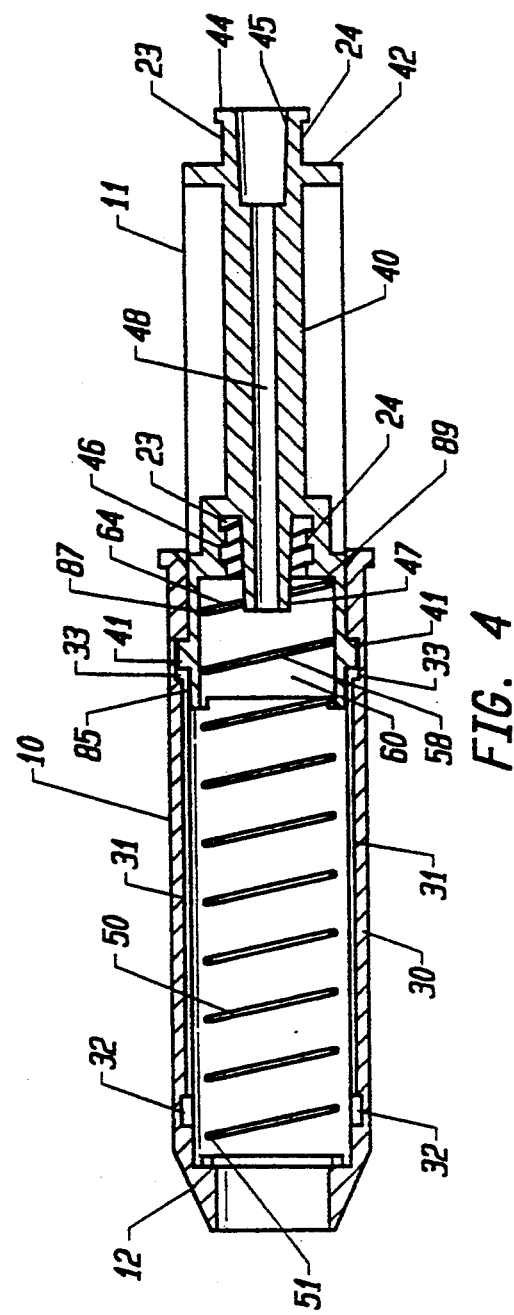

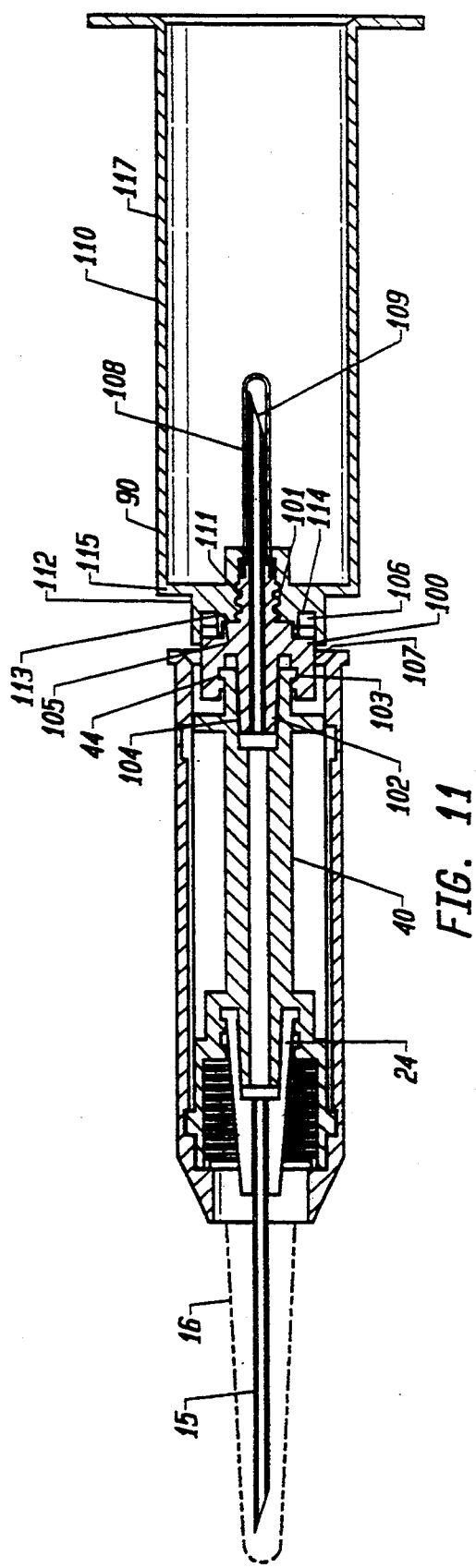
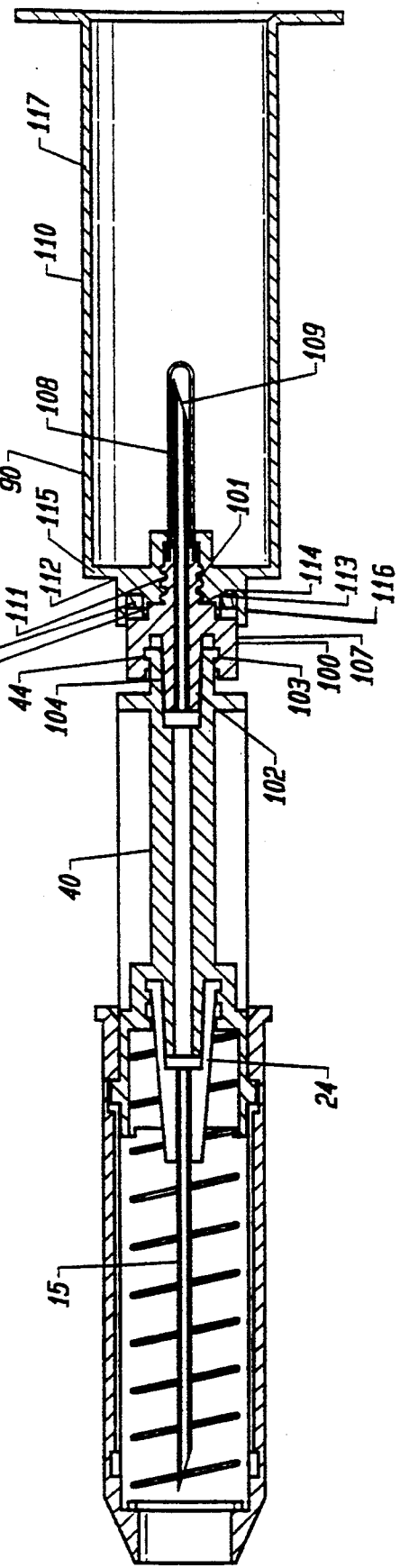

HYPODERMIC NEEDLE SAFETY DEVICE WITH SLIDING OUTER COVER

This is a division of application Ser. No. 07/967,651, filed Oct. 28, 1992, now U.S. Pat. No. 5,295,975.

FIELD OF THE INVENTION

The present invention relates generally to a safety apparatus for use with a standard hypodermic needle and syringe or other means for transferring fluid to or from a patient. More particularly, this invention is intended to protect care-givers and patients from accidental percutaneous needle penetrations ("sticks"), which can result from accidents that can occur when handling syringes, taking blood, and delivering medication.

A syringe consists of a hollow barrel with an internal plunger used either to force medication out of the discharge end or to apply a suction by which fluid can be withdrawn from the patient. At the discharge end of the syringe is a fitting, typically a Luer fitting, designed to connect a hollow bore hypodermic needle to the syringe. The needle is used to transfer the medication under the patient's skin. The hollow bore needle can also be used with a syringe to pull blood or other body fluids from the patient. Syringes come in many different sizes and are usually provided without a needle. This allows the care-giver to select an appropriate needle. Needles come in several different lengths, gages, and internal hole sizes.

A blood collection holder with a double-ended needle system is often used in place of a syringe to take blood samples from patients. One end of the double-ended needle is normally covered with a hard plastic cover prior to use. The needle at the opposite end has a thin rubber cover. This end is threaded into the closed end of the blood collection holder. When a blood sample is taken, the plastic cover is removed from the external needle, and the needle is inserted into the patient's vein. An evacuated tube with a rubber seal is then pushed into the blood collection holder. The needle pushes through the rubber cover and the vacuum in the tube draws the blood from the patient into the tube. After the blood sample has been taken, the tube is removed from the blood collection holder, and the needle is removed from the patient. At this point the double-ended needle assembly is removed from the blood collection holder and discarded.

Both in the case of injection of medication with a syringe and blood removal by a blood collection system, the moment the needle is removed from the patient, it is contaminated and potentially very dangerous. It can be a transmission vehicle for infectious diseases such as the human immunodeficiency virus (HIV) and hepatitis B infection, both of which are deadly.

For this reason, it would be desirable to provide devices and methods for preventing accidental penetration injuries to health care workers and others who handle used syringe or blood collection needles. It would be particularly desirable if the devices could be used with various types and sizes of existing needles and syringes having standard end connections. Additionally, it would be desirable if the devices were of simple construction, easy to use and not prone to failure. Finally, it would be desirable if the devices were constructed so as not to cover the measurement gradations that appear on the barrel of a syringe.

DESCRIPTION OF THE BACKGROUND ART

The prior art in the attempt to develop a device to protect care-givers from needle sticks includes U.S. Pat. No. 4,170,993 to Alvarez, which describes a sliding intravenous needle carrier assembly. This patent covers a different application than the present invention.

U.S. Pat. Nos. 4,425,120 to Sampson, 4,702,738 to Spencer, 4,723,943 to Spencer, and 4,693,708 to Wanderer all show needle protection systems. In each of these cases, the needle protection cover is designed to cover the syringe body. This increases the size of the syringe body and may cover or obscure the measurement graduations printed on the side of the syringe. Also in each of these cases, the syringe body must be modified to make the syringe cover function as intended. Standard syringes are not usable with these devices.

U.S. Pat. No. 4,966,592 to Burns is similar to the Sampson, Spencer '738, and Spencer '943 patents, in that the needle protection cover passes over the syringe barrel with the same disadvantages noted. It is different than the previous three patents in that it uses a spring to activate the needle cover and has an override feature. It has two major disadvantages. The first is that the device relies on the friction fit of a collar to hold the needle protection system in place on the syringe. The system can slip off and render the syringe unsafe. The second major disadvantage is that the pin that controls the device's operation passes through an open slot, so that the operator or a foreign object may interfere with the function of the safety system by obstructing the slot during operation.

The Jennings U.S. Pat. No. 4,693,708 shows a blood sampling system which has a needle cover that slides over the outside of a piston sleeve to cover the needle after the sample has been taken. The needle cover is manually operated and must be fully extended before the unit is completely safe.

U.S. Pat. No. 4,695,274 issued to Fox shows a needle hub with a protective cover mounted on a syringe. This device must be manually activated to uncover the needle for use. After use, the operator must manually push the outer cover to its locked position. Two embodiments of this device are shown. One embodiment has an external slot where the operator's hand or a foreign object can obstruct the safe operation of the device. In the other embodiment, the needle cover slides over the syringe barrel, thereby obstructing the graduations appearing on the barrel.

U.S. Pat. No. 4,804,371 to Vaillancourt shows a completely different concept, where the needle cover mounts on the hub of a needle which in turn is attached directly to a syringe. This device has a spring to push a small cap over the end of the exposed needle. This design does not lock in the safe position, and the needle cover is really only a guide to allow the operator to reinstall the original needle cap.

SUMMARY OF THE INVENTION

This invention is directed to a needle protection device and an improved blood collection system. The invention is designed to prevent patients, care-givers, and medical waste handlers from being exposed to injury and disease transmission from accidental needle penetrations ("sticks") by contaminated needles. The present invention improves on previous designs and corrects deficiencies in existing systems.

The needle protection device of the present invention is designed for use in combination with a hollow bore needle and a fluid reservoir. The needle may be selected from a wide range of standard, widely available hypodermic needles. The fluid reservoir will most commonly be a syringe but the invention may also be used with other means for transferring a fluid to or from a patient. The needle protection device of the present invention can also be used with a special needle as part of an improved blood collection system.

The device of the present invention comprises an extension section and a sliding outer cover to prevent the care-giver, or any subsequent person who handles the contaminated needle, from being stuck. One end of the extension connects to the syringe or other fluid reservoir. The needle connects to the other end of the extension. A narrow central channel passes through the length of the extension to convey fluid between the syringe and the needle.

The outer cover is slidable over the extension between two rest positions. The first position is the retracted position. This position allows for installation of the needle, for drawing medication into the syringe through the needle and for administration of an injection to the patient. The second rest position for the outer cover is the fully extended position. In this, the safe position, the outer cover is extended over the full length of the needle, thus preventing accidental injury or exposure to disease through an accidental needle stick.

The needle protection system can also be used as part of an improved and safer blood collection system. In this case, the needle at the front end of the extension is the same standard needle used for syringe applications. At the back of the extension, the needle stick prevention system is connected to additional components, including a special needle and blood collection holder, to operate as an improved blood collection system.

The present invention offers distinct advantages over existing designs. For example, it may be used with a full range of standard, commonly available needles and syringes. The device locks positively to the needle and to the syringe. The device is easy to use and its mechanism is not subject to inadvertent interference or blockage. Furthermore, use of this device will not obscure the measurement gradations appearing on existing syringes.

A preferred embodiment of the invention has a biasing means, preferably in the form of a helical spring, for urging the cover into the safe position. In some embodiments, locking means are provided to secure the cover in the extended position, the retracted position, or both. In a particularly preferred embodiment, an attempt on the part of an operator to remove the safety system from the syringe without first extending the outer cover will result in the spring automatically extending the cover over the needle.

BRIEF DESCRIPTION OF THE DRAWINGS

FIG. 1 is a drawing of the needle protection system in the fully retracted position mounted between a needle and a syringe;

FIG. 2 is a drawing of the needle protection system mounted between a needle and a syringe with the outer needle cover in the extended or safe position.

FIG. 3 is a sectional view of the needle protection system in the fully retracted position;

FIG. 4 is a sectional view of the needle protection system in the fully extended position;

FIG. 11 is a sectional view of the blood collection system showing a standard needle and the needle stick prevention system in the full retract position, connected to a special needle mounted to a blood collection holder; and FIG. 12 is a sectional view of the blood collection system showing a standard needle and the needle stick prevention system in the fully extended position, connected to a special needle mounted to a blood collection holder.

DETAILED DESCRIPTION OF SPECIFIC EMBODIMENTS

Figure 5:
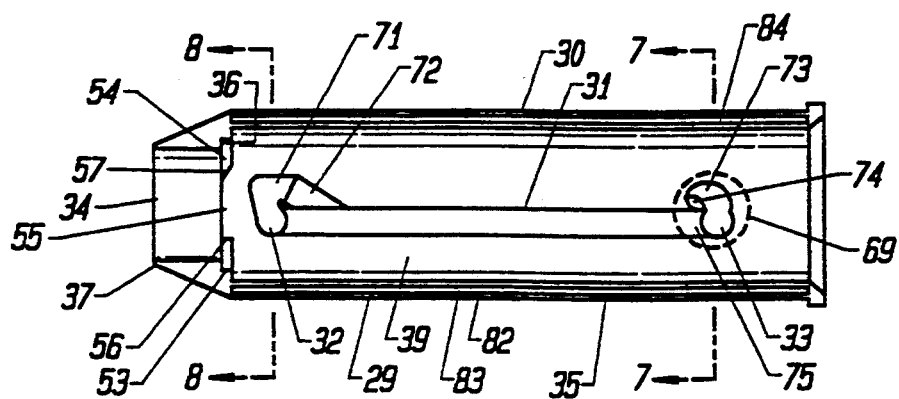
FIG. 5 is a view of the concave side of one half of the outer cover.

FIG. 1 and FIG. 2 show an external view of a needle protection system 10 with a back end 11 mounted to an interlocking connector 23 on a syringe 20, which consists of a barrel 21 and a plunger 22. The most popular interlocking connector 23 is known as a Luer lock 24. A front end 12 of needle protection system 10 is designed to accept a standard medical needle 15 which can be installed in a similar, but opposite interlocking connector 23. Am important safety design consideration of needle protection system 10 is that it allows needle 15 to be attached with its protective needle cover 16 in place. This prevents the care-giver from being accidentally stuck while connecting the needle and maintains the sterility of the needle until the system is ready for use.

FIG. 1 shows needle protection system 10 installed between needle 15 and syringe 20. In this configuration, the cover 16 of the needle can be removed to allow the care-giver to draw a desired dose of medication into syringe 20 through needle 15 and needle protection system 10. The needle is then inserted into the patient, the medication is injected, and the needle withdrawn. At this point, the needle is no longer sterile and may become a vehicle for the spread of the human immunodeficiency virus (HIV), hepatitis B infection or some other dangerous disease. The care-giver turns outer cover 30 on needle protection system 10 approximately 25 degrees counterclockwise and spring 50 provides a force to extend outer cover 30 until it locks at the fully extended position. FIG. 2 shows outer cover 30 locked over needle 15. The syringe, needle and needle protection system can now be properly and safely discarded.

FIG. 3 and FIG. 4 show two cross-sections of the needle protection system. FIG. 3 shows the outer cover retracted over extension 40 with spring 50 compressed. Guide pin 41 formed on extension 40 locks into front end retaining terminal 32 in channel 31. The channel is molded into the inside surface of outer cover 30. There are preferably two sets of pins 41 and channels 31 but a device having only one pin and channel would be functional. Also, it might be desirable in some cases to provide more than two pin and channel sets. It should also be appreciated that, although it is preferred that the pins be on the extension and the channel on the outer cover, a functional device according to the present invention could also have the pins on the interior of outer cover and the channel on the extension.

FIG. 4 shows the needle protection system with the outer cover in the fully extended position. In this case, spring 50 has pushed outer cover 30 to the fully extended position. At this position, pin 41 on extension 40 is engaged with back end retaining terminal 33 at the end of channel 31 opposite the front end retaining terminal. This locks outer cover 30 in the fully extended position where it completely covers the needle and protects the care-giver or other person handling the syringe against accidental injury or disease transmission.

Extension 40 has an interlocking connector 23, which attaches to the syringe 20. In FIG. 3 and FIG. 4, this connector 23 is shown as a Luer lock, a commonly used connector in the medical industry. On the back end 42 of extension 40 a female Luer lock 24 is used to connect to the male Luer lock on syringe 20. The connection is made by turning extension 40 clockwise with respect to syringe 20, so that the external threads 44 on extension 40 engage the internal threads (not shown) on syringe 20. This seats the male taper (not shown) on syringe 20 into the female taper 45 on extension 40.

At the front end 43 of extension 40, there is also an interlocking connection 23 which attaches to needle 15. Again, this connector is a Luer lock; however, it is the male type, which is compatible with standard needles used in the medical industry. The needle 15, with its plastic cover 16, is installed in extension 40 by turning the needle clockwise relative to extension 40. The needle's external threads (not shown) engage the internal threads 46 of extension 40. This seats the male taper 47 of the extension Luer lock into the needle to form a seal. Needle 15 should always be installed after the needle protection system is installed on the syringe 20.

As an alternative, the system could be manufactured and sold with a needle already in place, thus eliminating the need for the care-giver to install the needle. The system could also be manufactured with the needle fixed permanently or made integral with the front end of the extension.

Outer cover 30 can be molded as a single piece or as two pieces to be fastened together. If it is molded as one piece, channel 31 on the inside surface must be formed by a collapsing mandrel. This requires a complex mold. Channel 31 should not extend through the wall of outer cover 30. This is to prevent obstruction of the channel by the care-giver's hands or by some other object which might lodge in the channel.

The high cost of the complex mold with the collapsing mandrel and the potentially shorter life of the complex mold make it desirable to mold outer cover 30 in two halves and join the two halves together during assembly of the needle protection system.

FIG. 5 shows a view of a half section 35 of outer cover 30 and can be used to illustrate some of its important features. The front end 37 of outer cover 30 has an opening 34 which is concentric to the centerline of the outer cover and large enough to allow needle 15 to be installed with its plastic cover 16 in place. At the back of opening 34, a concentric shelf 36 is molded in which is located retention ring 53 for the front end 51 of spring 50. The walls 54 of spring retention ring 53 have two or more openings 55 which match projections 61 on the spring cavity 60 of extension 40. These openings have a vertical wall 56 on one side, and a sloped wall 57 on the other. When the outer cover is fully retracted, the projections 61 on extension 40 are interlocked with the openings 55. If the outer cover is turned clockwise, vertical wall 56 of opening 55 meets vertical wall 62 of extension projection 61. This causes outer cover 30 to turn extension 40 and seat Luer lock 24 onto syringe 20. Outer cover 30 can therefore be longer than extension 40. Extension 40 can be relatively short, yet still allow sufficient travel of outer cover 30 to cover needle 15.

If outer cover 30 is turned counterclockwise with respect to extension 40, then sloped wall 57 of spring retention ring 53 will meet sloped wall 63 of extension projection 61 and extension pin 41 will be released from front retaining terminal 32, thus allowing spring 50 to force outer cover 30 to the fully extended position. This is a safety feature of the needle protection system intended to prevent a care-giver from attempting to remove the needle protection device from a syringe 20 unless outer cover 30 is in the fully extended (safe) position covering needle 15.

The operation of the needle protection system is controlled by internal channels 31 in outer cover 30. These channels engage pins 41 on extension 40. Channels 31 use rotation of outer cover 30 with respect to extension 40 and elevation changes in channels 31 to control operation of needle protection system 10.

Referring to FIG. 5, with outer cover 30 in the full retract position, extension pins 41 will be locked in front end retaining terminals 32. The bottom of each retaining terminal is approximately 0.035 to 0.045 inches below inside surface 39 of outer cover 30. In order to release outer cover 30, the operator would turn the outer cover counterclockwise approximately twenty-five degrees to a point 71 with the same elevation. Releasing outer cover 30 will allow the spring 50 to push the outer cover 30 until the pins 41 engage a ramp 72 which changes the pin 41 elevation from 0.035 to 0.045 inches below the inside surface 39 of outer cover 30 to approximately 0.010 to 0.013 inches below the inside surface 39 of outer cover 30. The pins 41 then drop into channels 31 and change to 0.015 to 0.020 inches below the inside surface 39 of outer cover 30 while spring 50 continues to push outer cover 30 towards its fully extended position.

When pins 41 reach the end of channels 31, the pins drop into back end retaining terminals 33, which are approximately 0.035 to 0.045 inches deep. This locks outer cover 30 in the fully extended position. At this point needle 15 is fully covered and safe.

There are situations where it may be necessary to override needle protection system 10. One situation is when syringe 20 is filled with the medical dosage at a remote site from the patient, and the care-giver would like to extend outer cover 30 for protection during transit to the patient. Another is if syringe 20 is used to draw blood. In this case outer cover 30 will be extended over needle 15 after the blood sample is taken. At the laboratory, however, outer cover 30 is retracted, so that the blood sample can be removed from syringe 20 for analysis. Needle protection system 10 has a "fail-safe" override feature requiring the care-giver to use two hands to retract outer cover 30.

To retract outer cover 30, the care-giver must rotate outer cover 30 counterclockwise and push slightly against spring 50 until pins 41 move to point 73 in the back end retaining terminal 33. A small and narrow ramp 74 engages the edge of pins 41, and as the care-giver rotates outer cover 30 clockwise, ramp 74 raises pins 41 from approximately 0.035 to 0.045 inches below the inside surface 39 of outer cover 30 to approximately 0.015 to 0.020 inches below the inside surface 39 of outer cover 30. At this elevation pins 41 can be moved to position 75 which will allow the care-giver to pull outer cover 30 against spring 50 into the full retract position where pins 41 will lock into front end retaining terminals 32. At any point in the override process, if the care-give releases outer cover 30, spring 50 will return outer cover 30 to the fully extended and safe position.

Figures 7, 8:
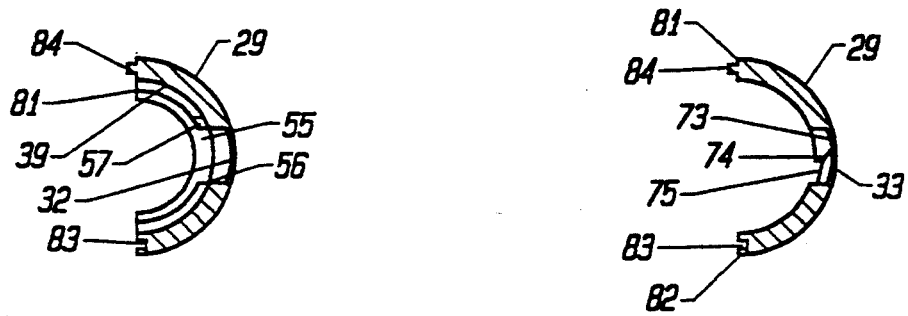
FIG. 7 is a sectional view of FIG. 5 through lines 7, 7 showing details of the locking pins.
FIG. 8 is a sectional view of FIG. 5 through lines 8, 8 showing details of the notches on the inside of the front end of the outer cover.

With outer cover 30 molded in two halves, channel 31 should be molded into the inside surface 39 as close to 90 degrees from the seam 81 between the two halves as possible. With front end retaining terminal 32 and back end retaining terminal 33 designed as shown, the total width of channel 31 should cover about 45 degrees of arc and be centered between seams 81 as shown in FIG. 7 and FIG. 8.

Needle protection system 10 has an extension 40 for connection to a syringe 20 with Luer lock 24 on back end 42. Extension 40 also attaches to needle 15 with Luer lock on front end 43. Extension 40 is used to convey the medication or other fluid between syringe 20 and needle 15. Extension 40 also carries pins 41 which control the position of outer cover 30. Extension 40 is made from molded plastic which is inert to medications and body fluids.

Figure 10:
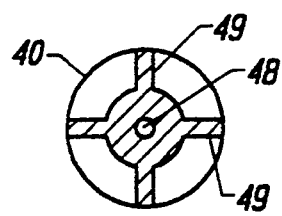
FIG. 10 is a sectional view of FIG. 6 through lines 10, 10 showing the extension stiffeners.

As depicted in FIG. 10, extension 40 has stiffeners 49 which provide the care-giver positive control over needle 15 while holding syringe 20. This minimizes the effect of increasing the overall length of the syringe 20 and needle 15 combination.

At the front end 43 of extension 40 and concentric to male Luer lock 24, there is a spring cavity 60 which retains back end 64 of spring 50. On the outside walls 85 of spring cavity 60, are two or more external pins 41 molded as an integral part of the extension. Pins 41 cooperate with channels 31 on the inside surface 39 of outer cover 30. Accordingly, pins 41 have a diameter just smaller than the width of channels 31.

Figure 6:
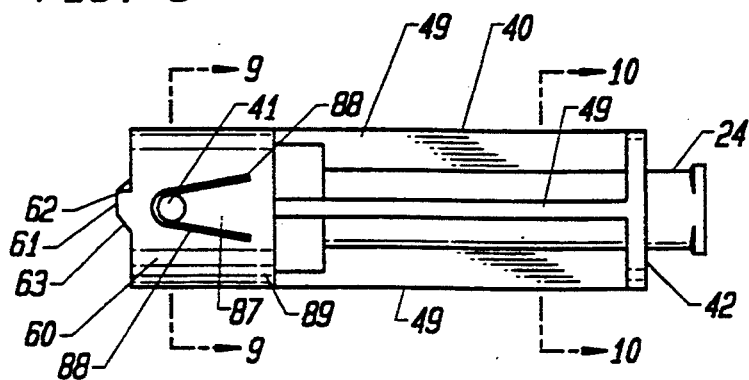
FIG. 6 is a view of the extension showing its stiffeners and part of the locking mechanism.
Figure 9:
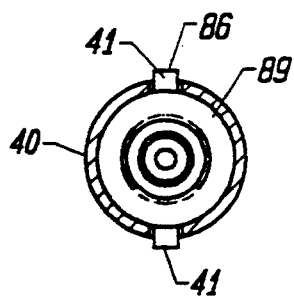
FIG. 9 is a sectional view of FIG. 6 through lines 9, 9 showing the details of the pins and the male Luer lock inside the spring cavity.

Pins 41 are located at the end of levers 87 which are made by cutting grooves 88 in the outside wall 85 of spring cavity 60. These grooves extend from the back wall 89 of spring cavity 60 out to pins 41, around a portion of the circumference of pin 41, and back to the back wall 89 of spring cavity 60. Grooves 88 can be parallel and spaced at distance equal to the diameter of the pin 41, or the grooves can separate as they approach the back wall 89 of spring cavity 60 as shown in FIG. 6. Levers 87 use the elasticity of the extension material to push pins 41 into the various elevations in channels 31 in the inside surface 39 of outer cover 30. The wider grooves 88 are cut into the outside wall 85 of spring cavity 60, the greater the levering effect on pins 41. Also, because pins 41 are on the external surface 85 of spring retention cavity 60, actuating spring 50 will be in contact with the back side of pin levers 87 and will act as a backup spring to insure that pins 41 are properly seated in channel 31. This is an additional safety feature of needle protection system 10.

As shown in FIG. 7 and FIG. 8, outer cover 30 is made from two pieces which will be fastened to each other during the assembly of needle protection system 10. The assembly process will start with the installation of spring 50 into spring cavity 60 on extension 40. Then extension 40 and spring 50 will be inserted in one half of outer cover 30. As spring 50 is compressed, pin 41 on extension 40 will engage front end retaining terminal 32. Then the second half of outer cover 30 will be placed over spring 50 and extension 40. Pin 41 will be located in front end retaining terminal 32 of the second half, and the two halves will be pressed together. Seam 81 between the two halves has an interlocking edge 82, which is used to align one side with the other. On one side the interlocking edge is a slot 83, and on the other side the interlocking edge is a ridge 84. The slot 83 and ridge 84 can also function as wave guides for a sonic welding process which can be used to join the two sides of outer cover 30.

Sonic welding is a process in which energy is used to melt the interface between two plastic parts and join them together. Without slot 83 and ridge 84, flashing would develop at seam 81 during the sonic welding process. The flashing could prevent the proper operation of the needle protection system. Accordingly, slot 83 and ridge 84 should extend down both sides of outer cover 30 for at least the entire length of travel along extension 40.

It should be noted that the sonic welding process will bond all similar plastic materials. Therefore, it is desirable for extension 40 and outer cover 30 to be formed of dissimilar plastic materials that will not bond with each other during the sonic welding process.

The outside surface 29 of outer cover 30 can be molded with a textured surface to make it easier for the care-giver to hold and manipulate. Outer cover 30 does not have to be round; however, it should be of sufficient wall thickness to accommodate the depth of channel 31. It may also have a clear window 69 on the outside surface 29 to allow the care-giver to see pin 41 in back end retaining terminal 33 in order to more easily operate the override feature.

The needle protection system can also be used as a blood collection system by adding two additional components as shown in FIG. 11 and FIG. 12. Blood collection system 90 consists of a needle 15 with a Luer lock 24 connected to extension 40. The needle is again a standard medical needle of the desired gage and length as selected by the care-giver. Luer lock 24 at the back of extension 40 connects to a special needle 100, which has an external dual helix thread 101 for connection to the internal dual helix thread 111 on hub 112 of blood collection holder 110.

Special needle 100, which mounts on the back of extension 40, has a male Luer lock 102 and an internal thread 103 to engage the external thread 44 on the back of extension 40 to seat and seal male taper 104 of Luer lock 102. Special needle 100 also has a sealing surface 105, which contacts an opposite sealing surface 113 on blood collection holder 110 when the external dual helix thread 101 of special needle 100 is fully engaged. Preferably, special needle 100 is equipped with one or more ratchets 106 molded into the special needle outside of sealing surface 105. Ratchets 106 engage with recessed teeth 114 in wall 115 of hub 112 of blood collection holder 110 when special needle 100 is fully seated. Special needle 100 also has a soft rubber cover 108 over the tip 109 of the needle to form a seal with a blood container (not shown) when special needle 100 is pushed through rubber cover 108 to insert the special needle into the blood container.

Blood collection holder 110 is specifically designed to be used once with special needle 100 and then discarded. When ratchets 106 engage with the recessed teeth 114, special needle 100 cannot be removed from blood collection holder 110. The recessed teeth are surrounded by a concentric wall 116 to prevent anyone from manually disengaging ratchets 106 from the teeth 114. Outer member 107 is positioned against the concentric wall 116 to enclose and prevent access to the teeth 114. Body 117 of blood collection holder 110 acts as a permanent cover over the used special needle 100 to protect the care-giver from a potentially dangerous needle stick.

Although the ratchet and tooth mechanism just described is the preferred means for preventing removal of the special needle from the blood collection holder, other mechanisms would work as well. For example, the special needle could be fixed to the blood collection holder with an appropriate bonding agent such as an adhesive. Alternatively, the blood collection holder and special needle could be made integral, with the blood collection holder being formed about the special needle. The only requirement is that the blood collection holder not be removable from the special needle.

The foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to which fall within the scope of this invention as defined in the claims.

What is claimed is:

1. A system for collecting fluid from a patient, the system comprising:
   an extension having front and back ends and a central cavity therethrough;
   a front end connection formed at the front end of the extension;
   a standard hypodermic needle connected to the front end connection;
   a back end connection formed at the back end of the extension;
   a special needle connected to the back end connection;
   a blood collection holder connected to the special needle and covering the special needle;
   an outer cover slidably disposed about the extension and shiftable between an extended position where the hypodermic needle is covered and a retracted position where the hypodermic needle is exposed; and
   a ratchet acting in conjunction with a plurality of teeth for preventing removal of the blood collection holder from the special needle, wherein the ratchet and teeth are surrounded by an enclosure to prevent access to the ratchet and teeth.

2. The fluid collection system of claim 1, wherein the special needle is made integral with the blood collection holder.

3. The device of claim 1, wherein the front end and the back end connections comprise luer lock connectors, whereby a variety of needle sizes can be connected thereto.

4. A method for preventing accidental injury from a hypodermic needle, the method comprising the steps of:
   connecting a fluid reservoir to an extension having an outer cover slidably disposed about the extension, the connection being formed by a ratchet acting in conjunction with a plurality of teeth;
   enclosing the ratchet and the teeth to prevent access to the ratchet and teeth;
   connecting the needle to the extension;
   sliding the outer cover into a position covering the needle.

5. The method of claim 4, further comprising locking the outer cover in the covered position until the cover is rotated to unlock the outer cover.

6. A system for collecting fluid from a patient, the system comprising:
   an extension having front and back ends and a central cavity therethrough;
   a front end connection formed at the front end of the extension;
   a standard hypodermic needle connected to the front end connection;
   a back end connection formed at the back end of the extension;
   a special needle connected to the back end connection;
   a blood collection holder connected to the special needle and covering the special needle;
   an outer cover slidably disposed about the extension and shiftable between an extended position where the hypodermic needle is covered and a retracted position where the hypodermic needle is exposed; and
   means for translating the outer cover from the retracted position to the extended position upon rotation of the outer cover when in the retracted position.

7. The device of claim 6 wherein the translating means comprises a spring.

8. The device of claim 6, further comprising means for locking the outer cover in the extended position until the cover is rotated.

* * * * *